United States Patent [19]

Otsuji et al.

[11] Patent Number: 5,032,311

[45] Date of Patent: Jul. 16, 1991

[54] DETERGENT COMPOSITION CONTAINING POLIANTHES L-DERIVED ACIDIC HETEROPOLYSACCHARIDE

[75] Inventors: Kazuya Otsuji, Utsunomiya; Yasuki Honda, Tochigi; Kikuhiko Okamoto, Koshigaya; Hakaru Inaoka, Utsunomiya; Satoshi Takano, Utsunomiya; Yukio Sugimura, Utsunomiya; Noriko Okamura, Tokyo; Kazumi Saito, Tokyo; Yoshinori Takema, Tokyo; Toshiyuki Suzuki, Ichikawa, all of Japan

[73] Assignee: KAO Corporation, Tokyo, Japan

[21] Appl. No.: 485,546

[22] Filed: Feb. 27, 1990

Related U.S. Application Data

[62] Division of Ser. No. 165,912, Mar. 9, 1988, Pat. No. 4,923,809.

[30] Foreign Application Priority Data

Mar. 9, 1987 [JP] Japan .................. 62-53768
Feb. 2, 1988 [JP] Japan .................. 63-22621

[51] Int. Cl.$^5$ .................. C11D 10/02; C11D 3/46; C11D 3/60
[52] U.S. Cl. .................. 252/174.17; 252/DIG. 5; 252/DIG. 13
[58] Field of Search .................. 252/174.17, DIG. 5, 252/DIG. 13

[56] References Cited

U.S. PATENT DOCUMENTS

| 3,923,782 | 12/1975 | Finn et al. | 252/174.17 |
|---|---|---|---|
| 4,061,585 | 12/1977 | Finn et al. | 252/174.17 |
| 4,304,906 | 12/1981 | Kang et al. | 536/114 |
| 4,364,837 | 12/1982 | Pader | 252/174.17 |
| 4,483,782 | 11/1984 | Cox et al. | 252/174.17 |
| 4,514,563 | 4/1985 | Fujiyama et al. | 536/123 |
| 4,575,551 | 3/1986 | Fujiyama et al. | 536/123 |

FOREIGN PATENT DOCUMENTS 2188060 9/1987 United Kingdom .

OTHER PUBLICATIONS

"Biological Abstracts", Feb. 15, 1983; 75(4); #29141.

*Primary Examiner*—Paul Lieberman
*Assistant Examiner*—A. Beadles-Hay
*Attorney, Agent, or Firm*—Oblon, Spivak, McClelland, Maier & Neustadt

[57] ABSTRACT

A novel acidic heteropolysaccharide which comprises as its structural units arabinose, mannose, galactose, glucuronic acid, and xylose, at a specific ratio. The polysaccharide can be prepared by culturing a callus induced from a plant belonging to the genus Polianthes L. in a culture medium containing plant hormones. The polysaccharide can be used as a component of agents for external application and detergents, and provides good moisturizing effects and a smooth, satisfying feeling upon use. When formulated in detergents, they produce remarkable improvement in a clean, rich feeling upon use.

7 Claims, 2 Drawing Sheets

DETERGENT COMPOSITION CONTAINING POLIANTHES L-DERIVED ACIDIC HETEROPOLYSACCHARIDE

This is a division of application Ser. No. 07/165,912, filed on Mar. 9, 1988, now U.S. Pat. No. 4,923,809.

BACKGROUND OF THE INVENTION

1. Field of the Invention

This invention relates to novel acidic heteropolysaccharides and also to a process for preparing such acidic heteropolysaccharides by plant-tissue culture method.

2. Description of the Background

Polysaccharides induced from plants are widely utilized as a viscosity increasing agent, gelatinization agent, foam stabilizer, suspension or emulsion stabilizer, capsule forming agent, adhesives, bioactive agent, and the like.

Conventionally, these polysaccharides are commonly produced from seeds, fruits, stems, trunks, leaves, roots, tubers, or tuberous roots of naturally grown or artificially cultivated plants by tapping, extraction, or the like methods.

Production from the natural sources, however, is liable to be influenced by climatic conditions which tend to cause fluctuation in the production amount and price. Because of this, various trials have been undertaken in recent years to produce these polysaccharides from plants of natural origin by culturing calluses or organa of such plants artificially by means of plant-tissue culture method, thus eliminating the adverse influence of climatic conditions.

There are very few reports concerning the production of polysaccharides of plant origin by plant-tissue culture method application. It is known, however, in relation to research about cell wall development mechanism that small amounts of polysaccharides are secreted in a liquid culture broth wherein a callus is cultured. Reports indicate, for instance, that *Vinca rosea* L. produces 0.22 gm of polysaccharides per liter of culture broth in 10 days, *Glycine max* Merril produces 0.49 gm of polysaccharides per liter of culture broth in 8 days, and *Phaseolus vulgaris* L. produces 1.6 gm of polysaccharides per liter of culture broth in 21 days.

The conventionally utilized plant-tissue culture method, however, has a drawback in its extremely low rate of production. A strong desire has thus existed for the development of a plant-tissue culture method capable of a higher productivity.

In this situation, the present inventors have conducted extensive studies and found that a large amount of polysaccharides was produced by using plants belonging to the genus Polianthes L. as a plant source, and culturing the callus induced therefrom in a culture medium containing one or more plant hormones. The inventors further found that polysaccharides thus produced contained novel acidic heteropolysaccharides which were different from any polysaccharides which were conventionally known. Such findings have led to the completion of this invention.

SUMMARY OF THE INVENTION

Accordingly, one object of this invention is to provide a process for preparing an acidic heteropolysaccharide comprising culturing a callus induced from a plant belonging to the genus Polianthes L. in a culture medium containing one or more plant hormones and collecting the acidic heteropolysaccharide from the culture broth.

Another object of this invention is to provide an acidic heteropolysaccharide which comprises as its structural units arabinose, mannose, galactose, glucuronic acid, and xylose, with the following combination sequence and in the following ratio:

$$\text{Ara } 1 \xrightarrow{}:\xrightarrow{} 3 \text{ Ara } 1 \xrightarrow{}:\text{Gal } 1 \xrightarrow{}:\xrightarrow{} 3 \text{ Man } 1 \xrightarrow{}:\xrightarrow{} 4 \text{ GlcUA } 1 \xrightarrow{}:\text{Xyl } 1 \xrightarrow{}, =$$
$$\phantom{xxxxxxxxxxxxxxxxxxxxxxxxxxxxxxxxxxxxxx} 2 \phantom{xxxxxxxxxxxxx} 3$$
$$\phantom{xxxxxxxxxxxxxxxxxxxxxxxxxxxxxxxxxxxxxx} \uparrow \phantom{xxxxxxxxxxxxx} \uparrow$$

1.6–2.4:1.2–2.0:1.0–1.8:1.4–2.2:1.4–2.2:0.1–0.3;

and having a molecular weight of $1.0 \times 10^4 - 2 \times 10^7$.

Still another object of this invention is to provide an agent for external application comprising the above-mentioned acidic heteropolysaccharide as a component.

The other object of this invention is to provide a detergent composition comprising the above-mentioned acidic heteropolysaccharide as a component.

Other and further objects, features, and advantages of the invention will appear more fully from the following description.

DETAILED DESCRIPTION OF THE INVENTION AND PREFERRED EMBODIMENTS

The production of polysaccharides according to this invention comprises using a plant belonging to Polianthes L., culturing a callus induced from the plant in a culture medium containing one or more plant hormones, and collecting the polysaccharides from the culture broth.

A typical example of the plant belonging to Polianthes L. is *Polianthes tuberosa* L. Portions of the organ or tissue of the plant such as the flower, stem, leaves, bulb, roots, or the like are used as the explant. Among the most desirable portions is a certain tissue of the flower.

The basal media employed for inducing the callus may be those conventionally employed in plant-tissue culturing, and include Murasige-Skoog medium, Linsmaier-Skoog medium, Gamborg medium, White medium, Tuleeke medium, Nitsch & Nitsch medium, or the like.

It is imperative that one or more plant hormones be added to these media. Examples of the plant hormones to be employed are auxins such as 2,4-dichlorophenoxyacetic acid (2,4-D), α-naphthaleneacetic acid (NAA), and indoleacetic acid (IAA), indolebutylic acid (IBA), cytokinins such as furfurylaminopurine (kinetin), benzyladenine (BA), and dimethylallylaminopurine (2iP), and the like. Good results are obtained by the independent use of 2,4-D, or the combined use of NAA and BA, or NAA and kinetin. The concentrations of hormones required for inducing the callus are $5\times10^{-4}-1\times10^{-7}$ M for 2,4-D, when it is employed independently, and $5\times10^{-4}-1\times10^{-7}$ M for NAA, when employed in combination with BA or kinetin, wherein BA and kinetin are used at a concentration of $1\times10^{-4}-1\times10^{-7}$ M respectively.

In addition to the basal medium and the plant hormones, sugars are added to the culture medium as a carbon source for inducing the callus. Sugars that can be employed for this purpose include glucose, fructose, mannose, xylose, sucrose, rhamnose, fucose, starch, and the like. Among these, the most typically used sugar is sucrose.

Although either solid or liquid culture medium can be employed for inducing the callus, the usually employed medium is the solid one.

The callus thus induced can be subcultured over more than 10 generations, while maintaining the same form in the same medium in which it was originally induced. Culture media employed for subculturing are those containing Linsmaier-Skoog medium or Murasige-Skoog medium as a basal medium; 2,4-D at a concentration of $1\times10^{-4}-1\times10^{-7}$ M, or the combination of NAA and BA, both at a concentration of $1\times10^{-4}-1\times10^{-7}$ M as plant hormones; and glucose, fructose, mannose, xylose, sucrose, rhamnose, fucose, starch, or the like, most desirably, sucrose, at 1-6% based on the culture medium, as a carbon source.

For the production of polysaccharides from the callus, the callus is cultured in a solid medium such as an agar medium or in a liquid medium. Culturing in a liquid medium is generally more desirable.

As a basal medium, Murasige-Skoog medium, Linsmaier-Skoog medium, Gamborg medium, White medium, Tulecke medium, Nitsch & Nitsch medium, or the like, is employed. Among these, the most desirable media are Murasige-Skoog medium and Linsmaier-Skoog medium.

The kind and concentration of the plant hormones is related to the productivity of the polysaccharides. The kinds of the plant hormones employed are auxins such as 2,4-D, NAA, IAA, and IBA; cytokinins such as kinetin, BA and 2iP; and gibberellins such as gibberellin $A_3$ ($GA_3$) Among these, the independent use of 2,4-D or NAA, or the use of NAA and BA or kinetin in combination, is desirable for obtaining better results. The concentration of hormones is, $5\times10^{-4}-1\times10^{-7}$ M, preferably $5\times10^{-5}-5\times10^{-6}$ M for the independent use of 2,4-D or NAA, and for the combined use of NAA and BA or kinetin, the NAA's concentration of $1\times10^{-4}-1\times10^{-7}$ M, preferably $1\times10^{-4}-5\times10^{-6}$ M, and the concentration of BA or kinetin of $5\times10^{-5}-1\times10^{-9}$ M, preferably $1\times10^{-5}-5\times10^{-7}$ M, are used.

Glucose, fructose, mannose, xylose, sucrose, rhamnose, fucose, starch, or the like, is used as a carbon source. The kind of carbon source employed does not have any great effect on the production of the polysaccharides, and sucrose is most usually used. Although there is no significant relationship between the concentration of the carbon source and the amount of polysaccharides produced, the generally desirable concentration of the carbon source is 1-6%.

There is no specific limitation to the conditions of the culturing. It is usually desirable, however, to carry out the culturing by shake method at a temperature of 20°-30° C. for 15-30 days.

Polysaccharides are collected from the culture broth thus obtained by subjecting the culture broth to centrifugation or filtration to separate the cells therefrom, and condensing using a rotary evaporator or the like. Ethanol is then added to the condensate to obtain a precipitate, which is freeze-dried to give crude polysaccharides.

The polysaccharides precipitate thus prepared is purified by a method conventionally utilized for purifying a polysaccharide. For example, the crude polysaccharides are dissolved in water, centrifuged to completely eliminate the insoluble portions, and then subjected to dialysis, ionexchange, or the like means of purification.

The purified polysaccharides thus prepared contain novel heteropolysaccharides. When the purified polysaccharides are hydrolyzed using 2 N $H_2SO_4$ aqueous solution at 100° C. for 8 hours, subjected to thin-layer chromatography using an eluent of ethyl acetate/pyrimidine/acetic acid/water at a ratio of 5:5:1:3, and colored by means of an aniline/diphenylamine/acetone/phosphoric acid reagent, arabinose, mannose, galactose, glucuronic acid, and xylose are detected. Analysis of this polysaccharide by gas chromatography also confirms the existence of arabinose, mannose, galactose, glucuronic acid, and xylose as constituent sugars. Gas chromatography analysis of this polysaccharide after methylation by Hakomori method and hydrolysis revealed that the substance has the following sequence of combination in the following ratio of each component:

1.6–2.4:1.2–2.0:1.0–1.8:1.4–2.2:1.4–2.2:0.1–0.3

Also, it was found that 0-50% of the carboxylic group of uronic acid is present as the methyl ester. In addition, the polysaccharides of this invention are identified as acidic in nature because of their absorption by cation-exchange resins. Analysis by high performance liquid chromatography using TSK Gel 4000 PW, 5000 PW, and 6000 PW column (Trade Names, manufactured by Toyo Soda Co., Ltd.) revealed that the molecular weight of this substance is $1.0\times10^4-2.0\times10^7$.

The acidic heteropolysaccharides have the following physicochemical characteristics.

Solubility

Soluble in water, and insoluble in ethanol, ether, and acetone.

Color Reaction

Anthrone reaction: positive
Carbazole reaction: positive
Erson-Morgan's reaction: negative Color and Form Those precipitated from ethanol are white or gray-white powder. Those purified by dialysis, ion-exchange, and freeze-dried are white in color and cotton-like or fibrous in form.

Specific rotation $[\alpha]_D^{25}: 0 - +20 (C=1.0$ in an aqueous solution)

Infrared Spectrum

Figure 1:
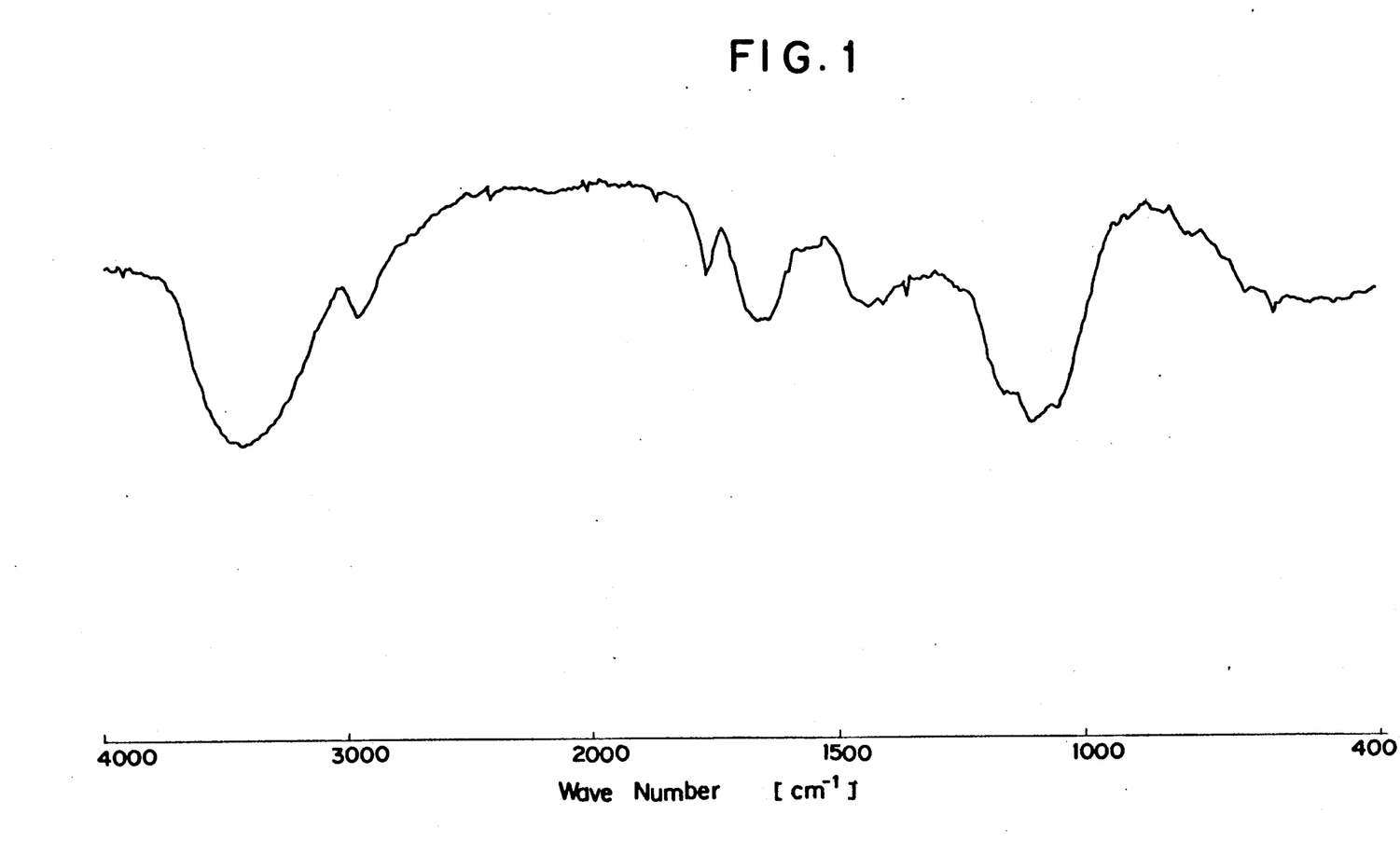
FIG. 1 is a drawing showing infrared spectrum of acidic heteropolysaccharides according to this invention.

Shown in FIG. 1.

Figure 2:
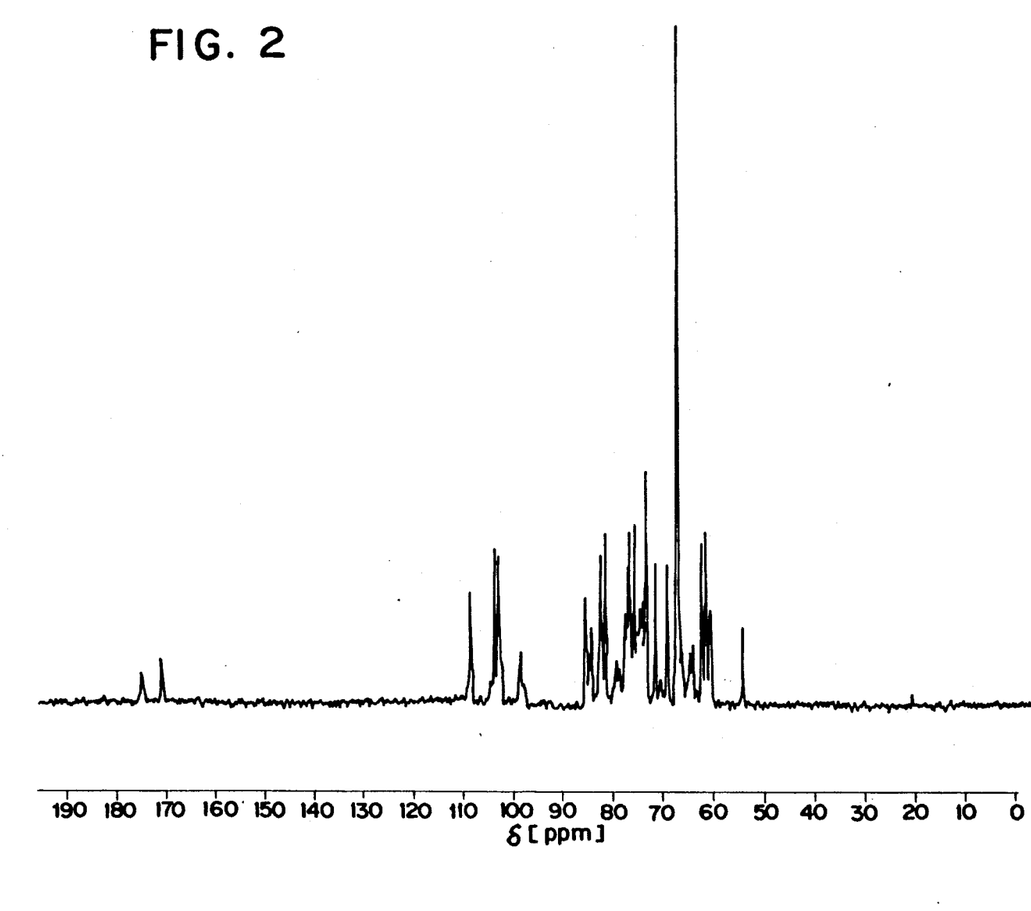
FIG. 2 is a drawing showing $^{13}C$ NMR spectrum of the same substance.

NMR Spectrum $^{13}C$ NMR spectrum is shown in FIG. 2 (eluent: $D_2O$; tube: 5 mm; internal standard: dioxane).

The acidic heteropolysaccharides of this invention have the following recurring unit:

wherein R is either of the following:

L - Ara 1→                                             (1)

D - Gal (1→3) Ara 1→                      (2)

D - Gal 1                                              (3)

L - Ara (1→3) - L - Ara 1→             (4)

Xyl 1→                                                (5)

and wherein the ratio of these elements is:

(1):(2):(3):(4):(5)=1.2–1.6:0.8–1.2:0.4–0.8:0.4–0.8:0.05–0.15

It is evident that the acidic heteropolysaccharides of this invention are novel in the art from their comparison with other polysaccharides. Specifically, there are known polysaccharides in the art which have the glucuronomannan structure [→2)-α-D-Man-(1→4)-β-D-GlcUA-(1→], contained in the acidic heteropolysaccharides of this invention. These polysaccharides are obtained from *Drosera capensis* (Channe et al., Carbohydr. Res., 113, 113-124, 1983), from Drosera binata (Channe et al., Phytochemistry, vol. 21, No. 9, 2297-2300, 1982), and from culture cells of *Nicotiana tabacum* (Mori et al., Carbohydr. Res., 91, 49-58, 1981; Akiyama et al, Agric. Biol. Chem., vol. 48, No. 2, 403-407, 1984), etc. Polysaccharides obtained from *Drosera capensis* and Drosera binata, however, are distinctly different from acidic heteropolysaccharides of this invention in that they have -2 Man 1- and -4 GlcUA 1- as their major bonds, and do not have -3 Ara 1-. The polysaccharide obtained from *Nicotiana tabacum* is also distinctly different from the acidic heteropolysaccharides of this invention. Specifically, it does not have the -3 Ara 1- bond as its major bond, according to the report by Channe et al; and according to the report by Akiyama et al., it has -4 GlcUA 1-, -2 Man 1- , and -5 Ara 1- as its major bonds, and again, does not have -3 Ara 1-. The acidic heteropolysaccharides of this invention are therefore novel polysaccharides which differ from any other polysaccharides conventionally known in the art.

The acidic heteropolysaccharides prepared according to the process of this invention have a variety of applications. For example, they can be used as a viscosity increasing agent, gelatinization agent, foam stabilizing agent, suspension or emulsion stabilizing agent, film forming agent, adhesives, bioactive agent, and the like.

Typical of such applications, agents for external application and detergent compositions, are hereinafter illustrated by way of examples. In the description given hereinbelow, the "acidic heteropolysaccharides" of this invention are from time to time referred to simply as "polysaccharides".

(1) Composition for external application:

The compositions for external application purpose can be grouped into medicines for skin application and cosmetics. The polysaccharides are formulated in the medicines for skin application in the amount of 0.0001–10% by weight ("% by weight" is hereinafter simply desgnated as "%"), and preferably 0.001–5%. If the amount is less than 0.0001%, the effect of this substance is not sufficiently exhibited. Various ointments containing medicinal ingredients are typical examples of the skin medicines. They may be those containing either oil-base substances, or oil-in-water- or water-in-oil-type emulsion base materials. There is no specific restriction as to the kinds of medicinal ingredients applicable. Analgestics, antiphlogistics, itchy killers, germicides, disinfectants, astringents, skin softeners, hormones, and the like may be employed as appropriate.

As for the cosmetics, the invented cosmetics may take various forms, such as oil-in-water- or water-in-oil-type cosmetics, creams, milky lotions, lotions, oily cosmetic, lip sticks, foundation, hair tonics, hair liquid or creams, hair growth agents, trichogens, and the like.

Oil ingredients which are suitably employed for preparing these agents for external applications are, for example, hydrocarbons such as liquid paraffin, paraffin wax, ceresine, squalane, and the like; waxes such as bees wax, sperm oil, carnauba wax, and the like; oils and fats of natural origin such as olive oil, camellia oil, jojoba oil, lanolin, and the like; silicone oil; fatty acids; higher alcohols; esters obtained from fatty acids and higher alcohols; and the like.

Surface active agents to be formulated in the agents for external application of this invention include polyoxyethylenealkyl ether, polyoxyethylene fatty acid ester, polyoxyethylenesorbitan fatty acid ester, polyoxyethylenesorbitol fatty acid ester, alkyl sulfate of polyoxyethylene hydrogenated castor oil, alkyl sulfate of polyoxyethylene, alkyl phosphate, polyoxyethylenealkyl phosphate, alkali metal salt of fatty acid, sorbitan fatty acid ester, glycerol fatty acid ester, and the like. In addition, various optional ingredients may be formulated in the agents for external application of this invention. Examples of such ingredients are viscosity adjusting agents, including polymeric compounds such as polyvinyl alcohol, carboxyvinyl polymers, carboxymethyl cellulose, polyvinyl pyrrolidone, hydroxyethyl cellulose, and methyl cellulose; naturally occurring gums such as gelatin and tragacanth gum; alcohols such as ethanol and isopropanol; humectants including propylene glycol, glycerol, 1,3-butylene glycol, dipropylene glycol, sorbitol, lactic acid, sodium lactate, sodium pyrrolidone carboxylate, and the like; and antiseptics including paraoxybenzoic acid ester, benzoic acid, sodium benzoate, sorbic acid, sodium sorbate, phenoxy ethanol, and the like.

(2) Detergent composition

The detergent compositions of this invention may be either in solid, liquid, or cream form. Typical detergents include shampoos, cleansing foams, body shampoos, soap cakes, and the like. To the detergent compositions comprising the polysaccharides of this invention, surface active agents are compounded in the amount of 50–99% for the compositions of the solid form, and 2–50% for the compositions of the liquid form or cream type. The amount of the polysaccharides of this invention to be added to the detergent composition is 0.001–10 parts by weight, and preferably 0.01–5 parts by weight, per 100 parts by weight of the surface active agents. With an amount of less than 0.001 parts by weight, it is difficult to impart the intended effect of the substance to the detergent composition. On the other hand, the addition in excess of 10 parts by weight is difficult in view of maintaining the compatibility of this substance with other ingredients.

Surface active agents that can be compounded to the detergent composition of this invention are any surface active agents conventionally used. These include anionic surface active agents such as alkylbenzene sulfonate, alkyl or alkenyl ether sulfate, alkyl or alkenyl sulfate, $\alpha$-olefin sulfonate, salt of a higher fatty acid (for soap cakes), alkyl or alkenyl ether carboxylic acid, salt or ester of $\alpha$-sulfofatty acid, amino acid-type surface active agents, and phosphate-type surface active agents; amphoteric surface active agents such as betaine, amidobetaine, sulfobetaine, hydroxysulfobetaine, amidoamino acid, and imidazoline-type surface active agents; nonionic surface active agents such as polyoxyethylenealkyl ether, polyoxyethylenealkyl ester, higher alcohol ether of polyglycerol, higher fatty acid ester of polyglycerol, alkylpolysaccharide, amine oxide, fatty acid alkylol amide; and cationic surface active agents such as monoalkyl ammonium salt, and the like.

Beside the essential ingredients mentioned above, various optional ingredients which are generally used in the conventional detergent compositions may be formulated into the detergent composition of this invention. Such optional ingredients include solvents such as water and lower alcohols, powders, oils, humectants, viscosity increasing agents, pH adjusting agents, antiseptics, antioxidants, vehicles, coloring materials, perfumes, any appropriate medicinal agents, and the like. They must, of course, be used to the extent and in the range which do not impair the effect of the invented detergent composition.

According to the present invention it is possible to prepare polysaccharides derived from plants, which have heretofore only been produced by extracting or tapping from naturally grown plants, by means of the plant-tissue culture method. This eliminates the requirement for a large field for preparing the polysaccharides and overcomes the greatest drawback of natural source, and price fluctuation due to changes in climatic conditions.

Also, the polysaccharides prepared according to this invention have excellent characteristics, and impart good moisturizing effects and a smooth, satisfying feeling upon use. When formulated in detergents, they produce remarkable improvement in a clean, rich feeling upon use.

Other features of the invention will become apparent in the course of the following description of the exemplary embodiments which are given for illustration of the invention and are not intended to be limiting thereof.

EXAMPLES

Example 1

Comparison of productivity of polysaccharides by liquid culture of the tuberosa callus and the callus of other plants:

(a) Callus Induction

A bud of tuberose 2–7 days before blossoming was taken, and sterilized in 70% ethanol for 1 minute and in 1% aqueous solution of sodium hypochlorite for 10 minutes, and then washed with sterilized water. The sterilized explant was cut into a suitable size and inoculated into a medium for callus induction. A tuber of an allium was sterilized in the same manner, its exodermis was removed, and the tuber was cut into pieces of a suitable size. The cut pieces were inoculated into a medium for callus induction. Tobacco was also sterilized in the same manner as applied to tuberose, and inoculated into a medium for callus induction. As for soybeans, the seeds were sterilized in 70% ethanol for 1 minute and in a 1% aqueous solution of sodium hypochlorite for 20 minutes, and then washed with sterilized water. The sterilized seeds were aseptically germinated and left to grow for 10 days until the embryonic axes had grown as high as 1 cm, whereupon the cotyledons and embryonic axes were cut from the germ-free seedings. The cotyledons and embryonic axes were than inoculated into a medium for callus induction.

Linsmaier-Skoog medium containing 0.8% agar was used for the basal callus induction medium. The plant hormones used were $10^5$ M NAA as auxin, and $10^6$ M BA as cytokinin. Sucrose in the amount of 3% based on the amount of the medium was added as the carbon source. After having been adjusted to pH 5.7 by 0.1 N KOH, the medium was sterilized for 15 minutes at 1.2 atmospheres. The cultivation was carried out under irradiation of electric light at a temperature of $25 \pm 1°$ C. Upon cultivation for 30–60 days calluses were found to have been induced from each explant.

(b) Subculture of callus

Each callus induced in (a) above was subcultured in the same medium as used for the callus induction under the same conditions. The callus was translated into a fresh medium once every 30 days.

(c) LIquid culture

Liquid Shake culture was carried out using the callus which had been cultured for 10 generations as in (b) above and the liquid medium having the same composition as the medium used in the subculture. Eighty (80) ml of medium was used in each 200 ml Erlenmyer flask. Into this medium 2 gm (fresh weight) of callus was inoculated, and was shake-cultured at a rotation of 120 rpm and at $25 \pm 1°$ C. for 30 days.

(d) Preparation of polysaccharide

Cells were removed from the culture broth obtained in (c) above by centrifugation or filtration, and the filtrate was condensed by rotary evaporator. To this condensate was added 3 folds in volume of ethanol, and the mixture was left to stand at 5° C. for 24 hours to obtain a precipitate, which was collected by means of centrifugation, washed with 70% ethanol, and freeze-dried to eliminate the water therefrom.

In the above procedure, extracelluler polysaccharides were prepared from 4 kinds of calluses. As shown in Table 1, the amount of polysaccharide produced by tuberose callus, 1.91 gm/1/30 days, is much higher than that produced by other calluses.

TABLE 1

| Production amount of extracelluler polysaccharides by calluses originated from different plants | |
|---|---|
| Kind of callus | Amount of polysaccharide produced (gm/1/30 days) |
| tuberose | 1.19 |
| tobacco | 0.66 |
| soy bean | 0.85 |
| garlic | 0.39 |

Among the polysaccharides thus produced, those originating from tuberose have the following characteristics:

Appearence: white—gray white powder
Sugar content (by phenol/sulfuric acid method and carbasol method): 80% (of which uronic acid is 25%)
Composing sugar: arabinose : mannose : galactose : xylose=10:5:4:1
Protein content: <2%
Water content: <5%
Molecular weight: 10,000–20,000,000

Example 2

Amount produced by different kinds of plant hormones:

Cultivation of tuberose callus with different kinds of plant hormones was conducted. The tuberose callus prepared in Example 1 was transplanted into liquid culture media each comprised of Linsmaier-Skoog medium. The Linsmaier-Skoog media contained $10^{-5}$ M NAA+$10^{-6}$ M BA, $10^{-5}$ M 2,4-D, $10^{-5}$ M NAA, $10^{-5}$ M IAA, and $10^{-5}$ M IBA. The cultivation was carried out under the same conditions as described in Example 1 (c). The quantity of medium used was 30 ml per 100 ml Erlenmyer flask. The polysaccharides were collected in the same method as described in Example 1.

As shown in Table 2, the production increased in the order of 2,4-D, NAA, NAA+BA, IBA, IAA. Among these, 2,4-D attained an especially high productivity of 3.60 gm/1/30 days.

TABLE 2

| Kinds of plant hormones vs. production of polysaccharides by tuberose calluses | |
|---|---|
| Plant hormones | Amount of polysaccharide produced (gm/1/30 days) |
| NAA ($10^{-5}$ M) | 2.65 |
| IAA ($10^{-5}$ M) | 1.01 |
| IBA ($10^{-5}$ M) | 1.25 |
| 2,4-D ($10^{-5}$ M) | 3.60 |
| NAA ($10^{-5}$ M) + BA ($10^{-6}$ M) | 1.91 |

Example 3

Concentrations of 2,4-D and NAA +BA, and production of polysaccharides:

Tuberose callus was cultured in varying concentrations of plant hormones. Tuberose callus prepared according to the methods described Example 1 (a) and (b) was transplanted into liquid culture media comprised of Linsmaier-Skoog medium containing plant hormones with varying concentrations, i.e., $5\times10^{-4}$ to $1\times10^{-6}$ M for 2,4-D, $1\times10^{-4}$ to $1\times10^{-6}$ M of NAA and $1\times10^{-5}$ M to $1\times10^{-7}$ M of BA for the NAA and BA combination. The media were cultured under the same conditions as described in Example 1 (c). Polysaccharides were collected according to the procedure as described in Example 1 (d). As seen from Table 3, in cultivation at concentrations of 2,4-D in the range of $5\times10^{-4}$ to $1\times10^{-6}$ M, the polysaccharides production is high at the concentrations of $5\times10^{-5}$–$5\times10^{-6}$ M, and is exceptionally high (3.41 gm/1/30 days) at the concentration of $1\times10^{-5}$ M. As for the combined use of NAA and BA, as shown in Table 4, polysaccharides production was highest at $1\times10^{-4}$ M NAA+$1\times10^{-5}$ M BA.

TABLE 3

| Concentration of 2,4-D vs. production of polysaccharides by tuberose calluses | |
|---|---|
| Concentration of 2,4-D (M) | Amount of polysaccharide produced (gm/1/30 days) |
| $5\times10^{-4}$ M | 1.26 |
| $1\times10^{-4}$ M | 1.53 |
| $5\times10^{-5}$ M | 2.73 |
| $1\times10^{-5}$ M | 3.41 |
| $5\times10^{-6}$ M | 1.90 |
| $1\times10^{-6}$ M | 0.75 |

TABLE 4

| Concentrations of NAA and BA vs. production of polysaccharides by tuberose calluses | | | |
|---|---|---|---|
| Concentration of BA | Concentration of NAA | | |
| | $1\times10^{-4}$ M | $1\times10^{-5}$ | $1\times10^{-6}$ M |
| $1\times10^{-5}$ M | 3.27 | 1.82 | 0.38 |
| $1\times10^{-6}$ M | 2.53 | 1.90 | 0.76 |
| $1\times10^{-7}$ M | 2.14 | 2.11 | 0.51 |
| | Amount of polysaccharide produced (gm/1/30 days) | | |

Example 4

Separation of acidic heteropolysaccharides from tuberose polysaccharides:

Tuberose polysaccharides, weighing 2 gm, which were prepared according to the method in Example 1, were dissolved in 400 ml of water and dialyzed for 24 hours using a cellulose tube for dialysis (manufactured by Union Carbide Corp.). The internal fluid was passed through a Sephadex A-25 ($CH_3COO^-$ type manufactured by Pharmacia Co.) column (length: 70 cm; diameter: 6 cm), which was then washed with 2 liters of water, and the intended substances were eluted with 0.5 M acetic acid buffer solution (pH 6.0). The eluted fractions were condensed and dialyzed using the same cellulose tube as used in the above dialysis. The internal fluid was again condensed, and freeze-dried to obtain 1.5 gm of acidic heteropolysaccharides having the same physicochemical characteristics mentioned above.

The major peaks in the $^{13}C$ NMR spectrum in ppm of this substance were as follows:

174.8, 170.9, 108.8, 103.9, 103.2, 102.5, 98.9, 85.5, 84.9, 84.4, 82.7, 81.7, 79.5, 78.9, 77.6, 77.2, 76.8, 75.9, 74.8, 74.4, 73.6, 71.8, 69.4, 66.5, 64.9, 64.4, 62.5, 61.7, 60.8, 54.4.

Example 5

Lotions

Lotions of the following formulation were prepared according to the following method. The moisture retaining effect and the degree of satisfaction upon use of these lotions were evaluated. The results are shown in Table 5.

| (Formulation) | Invented lotion | Comparative lotion |
|---|---|---|
| (1) acidic heteropolysaccharides (prepared from tuberose in Example 1) | 0.5% | — |
| (2) 1,3-butylene glycol | 2.5% | 2.5% |
| (3) glycerol (86%) | 0.5% | 0.5% |
| (4) polyoxyethylene hydrogenated castor oil (EO 40) | 0.5% | 0.5% |
| (5) lactic acid | 0.05% | 0.05% |
| (6) sodium lactate | 0.7% | 0.7% |
| (7) ethanol | 7.0% | 7.0% |
| (8) methyl paraben | 0.1% | 0.1% |
| (9) perfume | 0.05% | 0.05% |
| (10) purified water | 88.1% | 88.6% |

Preparation

Ingredients (1), (2), (3), (5), and (6) were added to purified water at an elevated temperature, and then cooled to room temperature. To this solution were slowly added ingredients (4), (8), and (9), which were dissolved in ethanol, and the obtained solution was filtered to give the lotion as a filtrate.

Evaluation of moisture retention

In order to evaluate the moisture retaining effect of the invented and comparative lotions prepared in the above, these products were applied to the forearm of the subjects in an amount each of 20 μ¼ cm². After 1 hour, the water content in the horny layer was measured (N=5; the instrument used: SKICON-200 manufactured by IBS Co.).

Organoleptic evaluation

Organoleptic evaluation of the invented lotion and comparative lotion, in terms of their smoothness on use, consistency of the smoothness, stickiness, and dampishness, was conducted using 20 women aged 20–35. The results are shown in Table 6, in which the values designate the percentage of the number of women who favorably responded to each of the evaluation items.

TABLE 5

| (Results) (1) Moisture retention | |
|---|---|
| Lotion applied | Relative value of water content of horny layer |
| Control | 1.00 |
| Invented lotion | 1.62 |
| Comparative lotion | 1.43 |

Water content of the body portion to which the invented lotion was applied was indicated as being higher than that to which the comparative lotion was applied. This confirms the high moisture retaining effect of the lotions to which the polysaccharides originated from tuberose is formulated.

TABLE 6

| (2) Organoleptic evaluation | Invented lotion | Comparative lotion |
|---|---|---|
| Smoothness on use | 100 | 0 |
| Persistence of the | 90 | 5 |
| smoothness | | |
| Stickiness | 35 | 20 |
| Dampishness | 60 | 15 |

The invented lotions into which the polysaccharides originated from tuberose were formulated exhibited remarkable smoothness on use and persistence. In addition, the lotion provided excellent dampishness to users, and yet was less sticky.

Example 6

Milky Lotion

A milky lotion of the following formulation was prepared according to the following method.

| (Formulation) | |
|---|---|
| Ingredients | Proportion (%) |
| (1) liquid paraffin | 4.0 |
| (2) squalane | 4.0 |
| (3) cetanol | 0.5 |
| (4) stearic acid | 1.5 |
| (5) sorbitan monooleate | 1.0 |
| (6) polyoxyethylenesorbitan monooleate (EO 20) | 1.0 |
| (7) glycerol momostearate | 0.5 |
| (8) ethyl paraben | 0.2 |
| (9) glycerol | 3.0 |
| (10) 1,3-butylene glycol | 5.0 |
| (11) acidic heteropolysaccharides (Prepared in Example 1 from tuberose) | 0.3 |
| (12) perfume | 0.05 |
| (13) purified water | 78.95 |

Preparation

Oil phase components (1)–(8) and (12) were heated and mixed until dissolved, and maintained at 70° C. Ingredients (9)–(11) were dissolved in purified water at an elevated temperature to obtain the water phase, which was slowly added to the oil phase and emulsified. The emulsion was gradually cooled to give the milky lotion.

Example 7

Cream

A cream of the following formulation was prepared according to the following method.

| (Formulation) | |
|---|---|
| Ingredients | Proportion (%) |
| (1) petrolatum | 8.0 |
| (2) lanolin | 2.0 |
| (3) squalane | 20.0 |
| (4) cetanol | 5.0 |
| (5) glycerol momostearate | 2.0 |
| (6) polyoxyethylenesorbitan monolaurate (EO 20) | 2.0 |
| (7) ethyl paraben | 0.2 |
| (8) acidic heteropolysaccharides (Prepared in Example 1) | 0.5 |
| (9) glycerol (86%) | 5.0 |
| (10) 1,3-butylene glycol | 5.0 |
| (11) perfume | 0.1 |
| (12) purified water | 50.2 |

Preparation

Oil phase components (1)–(7) and (11) were heated and mixed until dissolved, and maintained at 70° C. Ingredients (8)–(10) were dissolved in purified water at an elevated temperature to obtain the water phase. The oil phase was added to the water phase while stirring. The resulting mixture was treated by homogenizer, and chilled to obtain the cream.

Example 8

Pack

A pack of the following formulation was prepared according to the following method.

| (Formulation) | | |
|---|---|---|
| | Ingredients | Proportion (%) |
| (1) | polyvinyl alcohol | 18.0 |
| (2) | polyethylene glycol | 2.0 |
| (3) | 1,3-butylene glycol | 5.0 |
| (4) | acidic heteropolysaccharides (Prepared in Example 1) | 0.5 |
| (5) | ethanol | 8.0 |
| (6) | methyl paraben | 0.1 |
| (7) | perfume | 0.05 |
| (8) | purified water | 66.35 |

Preparation

Ingredients (2), (3), (4) and (6) were added to purified water while stirring until dissolved. To this solution was added polyvinyl alcohol, and the mixture was heated and agitated, and then ethanol in which perfume was dissolved was added and the entire mixture was dissolved to give the pack.

Example 9

Essence

An essence of the following formulation was prepared according to the following method.

| (Formulation) | | |
|---|---|---|
| | Ingredients | Proportion (%) |
| (1) | acidic heteropolysaccharides (Prepared in Example 1) | 1.0 |
| (2) | 1,3-butylene glycol | 20.0 |
| (3) | glycerol (86%) | 15.0 |
| (4) | polyethylene glycol | 5.0 |
| (5) | polyoxyethylenehexadecyl ether (EO 20) | 0.1 |
| (6) | citric acid | 0.05 |
| (7) | sodium citrate | 0.5 |
| (8) | methyl paraben | 0.2 |
| (9) | perfume | 0.1 |
| (10) | purified water | 58.05 |

Preparation

Ingredients (1)–(8) were dissolved in purified water, to which was added ingredient (9) and dissolved to give the essence.

Example 10

Face Cleansers

Face cleansers of the following formulations were prepared according to the following method. Cleansing performance and the degree of satisfaction of the products were evaluated, the results of which are shown in Table 7.

| (Formulation) | | | |
|---|---|---|---|
| | | Invented product | Comparative product |
| (1) | lauryl phosphate | 15.0% | 15.0% |
| (2) | lauric acid | 5.0% | 5.0% |
| (3) | triethanolamine | 23.0% | 23.0% |
| (4) | propylene glycol | 5.0% | 5.0% |
| (5) | distearic acid ethylene glycol | 3.0% | 3.0% |
| (6) | ethanol | 10.0% | 10.0% |
| (7) | perfume | 0.5% | 0.5% |
| (8) | acidic heteropolysaccharides (Prepared from tuberose in Example 1) | 1.5% | — |
| (9) | purified water | 37.0% | 38.5% |

Preparation

Ingredient (3) was added to the mixed solution of ingredients (1), (4) and (9) at an elevated temperature. To this mixture was added ingredients (2), (5), (6), (7) and (8), and mixed while heating until dissolved. The solution was cooled to give the liquid face cleansers.

Evaluation

Evaluation of the invented and comparative products concerning the items listed in Table 7 was conducted using women aged 20–35. The resulting designate the percentage of the number of women who favorably responded to each of the evaluation items.

TABLE 7

| | Invented product | Comparative product |
|---|---|---|
| Detergency | 35 | 30 |
| Lathering | 20 | 25 |
| Rinsing performance | 15 | 25 |
| Smoothness to the skin on use | 100 | 0 |
| Satisfaction after use (Dampishness) | 70 | 10 |

The invented face cleanser into which the polysaccharides originated from tuberose were formulated did not exhibit any functional decrease in detergency, lathering property, or rinsing performance, which are inherently required characteristics of a detergent, and also provided good satisfactory feeling to the skin during and after use.

Example 11

Cleansing foam

A cleansing foam of the following formulation was prepared according to the following method.

| (Formulation) | | |
|---|---|---|
| | Ingredients | Proportion (%) |
| (1) | lauryl phosphate | 30.0 |
| (2) | lauric acid | 2.0 |
| (3) | propylene glycol | 10.0 |
| (4) | distearic acid ethylene glycol | 3.0 |
| (5) | antiseptic | 0.3 |
| (6) | perfume | 0.5 |
| (7) | sodium hydroxide | 11.0 |
| (8) | acidic heteropolysaccharides (Prepared from tuberose in Example 1) | 1.0 |

-continued

| (Formulation) | |
|---|---|
| Ingredients | Proportion (%) |
| (9) purified water | 42.4 |

Preparation

To the heated mixed solution of ingredients (1), (3) and (9) was added ingredient (7), and then ingredients (2), (4), (5), (6) and (8) were added. The mixture was dissolved while heating, and cooled to give the cleansing foam.

The product provided smoothness and an excellent detergency on use. In addition it gave satisfaction after use without a rough, drawn out feeling.

Example 12

Shampoo

A shampoo of the following formulation was prepared according to the following method.

| (Formulation) | |
|---|---|
| Ingredients | Proportion (%) |
| (1) sodium polyoxyethylene lauryl sulfate | 16.0 |
| (2) lauric acid diethanolamide | 4.0 |
| (3) propylene glycol | 2.0 |
| (4) acidic heteropolysaccharides (Prepared from tuberose in Example 1) | 2.0 |
| (5) perfume | 0.5 |
| (6) purified water | 75.5 |

Preparation

Ingredient (4) was added to purified water, followed by the mixture of ingredients (1), (2), (3) and (5), and heating and dissolving. The mixture thus obtained was cooled to give the shampoo.

The product provided a high degree of satisfaction on use in terms of the slipperiness of hair, lathering, and rinsing performance.

Example 13

Soap cake

A soap cake of the following formulation was prepared according to the following method.

| (Formulation) | |
|---|---|
| Ingredients | Proportion (%) |
| (1) soap substrate | 97.0 |
| (2) titanium dioxide | 1.0 |
| (3) acidic heteropolysaccharides (Prepared from tuberose in Example 1) | 1.0 |
| (4) perfume | 1.0 |

Preparation

Ingredients (2), (3) and (4) were added to ingredient (1) and kneaded. The mixture was extruded by a plotter to provide a cake bar, which was cast into soap cakes.

The product produced smoothness on use with good lathering property and a high degree of detergency.

Example 14

Body shampoo

A body shampoo of the following formulation was prepared according to the following method.

| (Formulation) | |
|---|---|
| Ingredients | Proportion (%) |
| (1) lauryl phosphate | 10.0 |
| (2) coconut oil fatty acid potassium salt | 5.0 |
| (3) lauric acid | 5.0 |
| (4) triethanolamine | 15.0 |
| (5) 1,3-butylene glycol | 5.0 |
| (6) distearic acid ethylene glycol | 2.0 |
| (7) ethanol | 5.0 |
| (8) perfume | 0.5 |
| (9) acidic heteropolysaccharides (prepared from tuberose in Example 1) | 1.5 |
| (10) purified water | 51.0 |

Preparation

To the heated mixture of ingredients (1), (5) and (10), was added ingredient (4), followed by ingredients (2), (3), (6) and (9), all of which were dissolved while heating. The solution thus obtained was cooled and ingredients (7) and (8) were finally added. This was then agitated until dissolved to produce the liquid body shampoo.

The product provided a high degree of satisfaction in terms of slipperiness during use and dampishness of the skin after use.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by letters patent is:

1. A detergent composition comprising: an acidic heteropolysaccharide which comprises as its structural units arabinose, mannose, galactose, xylose, and glucuronic acid, and which is induced from a plant belonging to the genus Polianthes L., and a surface active agent.

2. The detergent composition according to claim 1, wherein the plant belonging to the genus Polianthes L. is *Polianthes tuberosa* L.

3. The detergent composition according to claim 1 or 2, wherein the acidic heteropolysaccharide is prepared by tissue culture method.

4. A detergent composition comprising:
   an acidic heteropolysaccharide which comprises at its structural units arabinose, mannose, galactose, xylose, and glucuronic acid, and which is induced from a plant belonging to the genus Polianthes L., and
   a surface active agent wherein the amount of acidic heteropolysaccharide to be added to the composition is 0.001–10 parts by weight per 100 parts by weight of the surface active agent.

5. The detergent composition according to claim 4, wherein the plant belonging to the genus Polianthes L. is *Polianthes tuberosa* L.

6. The detergent composition according to claim 4, wherein the acidic heteropolysaccharide is prepared by tissue culture method.

7. The detergent composition according to claim 5, wherein the acidic heteropolysaccharide is prepared by tissue culture method.

* * * * *